United States Patent [19]

Schneider

[11] 4,022,837

[45] May 10, 1977

[54] PRODUCTION OF KETONES FROM ALKENES, HYDRATED MOLYBDENUM(VI) OXIDE AND WATER

[75] Inventor: Ronald Alan Schneider, Richmond, Calif.

[73] Assignee: Chevron Research Company, San Francisco, Calif.

[22] Filed: Mar. 31, 1975

[21] Appl. No.: 563,742

Related U.S. Application Data

[63] Continuation-in-part of Ser. No. 49,561, July 24, 1970, abandoned.

[52] U.S. Cl. .......................................... 260/597 R
[51] Int. Cl.² ........................................ C07C 45/02
[58] Field of Search .................... 260/597 R, 586 P

[56] References Cited

UNITED STATES PATENTS

| | | | |
|---|---|---|---|
| 2,874,191 | 2/1959 | Foreman et al. | 260/597 |
| 3,255,238 | 6/1966 | Roelen et al. | 260/597 |
| 3,419,618 | 12/1968 | Hirseh et al. | 260/597 |

*Primary Examiner*—James O. Thomas, Jr.
*Assistant Examiner*—A. Siegel
*Attorney, Agent, or Firm*—Dix A. Newell; John Stoner, Jr.; W. Keith Turner

[57] ABSTRACT

A process is set forth for the production of ketones by the action of water and a hydrated molybdenum(VI)-oxygen compound upon an alkene feed. The reaction occurs in the range from 200° to 400° C.

11 Claims, No Drawings

PRODUCTION OF KETONES FROM ALKENES, HYDRATED MOLYBDENUM(VI) OXIDE AND WATER

CROSS-REFERENCE TO RELATED APPLICATION

This application is a continuation-in-part of U.S. application Ser. No. 49,561, filed July 24, 1970 now abandoned.

BACKGROUND OF THE INVENTION

This invention relates to a process for the production of ketones, more particularly to the conversion of an alkene to a ketone by treatment with hydrated molybdenum (VI) oxide and water.

Ketones are well known and have many uses. The individual ketones and molecular mixtures as prepared by the subject invention are in general useful as solvents in the chemical and manufacturing arts.

U.S. Pat. No. 3,255,238 to Roelen et al discloses a process for the production of materials such as $C_4$ and lower aldehydes, ketones, etc., by contacting propylene or isobutylene with oxygen in the presence of a catalyst consisting essentially of molybdenum oxide-phosphoric acid-boric acid.

U.S. Pat. No. 3,419,618 to Hirsch et al discloses a process for preparing acetaldehyde from ethylene by reacting ethylene with oxygen in the presence of a palladium oxide catalyst.

U.S. Pat. No. 2,874,191 to Foreman et al discloses a process for producing acetone from propylene by contacting the propylene in the absence of molecular oxygen with a composition comprising bismuth phosphomolybdate on a support selected from alumina and alumina-silica. According to the disclosure, preferably the reaction is carried out in the presence of water. According to the Foreman disclosure, the bismuth phosphomolybdate has the formula:

where: $x$ may be 1 to 12; $y$ may be 1 to 6; $z$ may be 40 to about 88; and any compound within this formula is suitable.

Hucknall et al, in "Selective Oxidation of Hydrocarbons", Academic Press (1974), discuss the use of bismuth oxide-molybdenum oxide ($Bi_2O_3$–$MoO_3$) as catalyst for the oxidation of hydrocarbons — for example, the oxidation of propylene to acrolein (propenal). Hucknall et al point out at page 32 that molybdenum oxide has a low activity compared to the bismuth oxide-molybdenum oxide catalyst and, in fact, has a lower activity than bismuth oxide has in reactions such as oxidation of propylene.

SUMMARY OF THE INVENTION

According to the present invention, a process is provided for the conversion of an alkene to a ketone which comprises contacting, at a temperature between about 200° and 400° C, a mixture consisting essentially of water and said alkene with a composition consisting essentially of a hydrated molybdenum(VI)-oxygen compound wherein said alkene is a gas or liquid at said temperature and wherein the carbon-carbon double bond carbon atoms of said alkene are both secondary carbons or one is secondary and the other is primary carbon, and wherein said mixture has a mol ratio of water to alkene between about 1:1 and 100:1.

Preferred reaction temperatures are between about 250° and 350° C, and preferably for each mol of alkene in the mixture an amount of water in the range from 1 to 100, preferably 3 to 10, mols is employed.

In a batch process, the mol ratio of the molybdenum-oxygen compound to olefin is desirably in the range 0.1:1 to 100:1, preferably 0.5:1 to 5:1. For a continuous process, a weight hourly space velocity (WHSV, weight of olefin feed per weight of the molybdenum-oxygen compound per hour) in the range 0.1 to 10 hours$^{-1}$ is satisfactory. One or more alkenes ($C_nH_{2n}$) of the formula RCH=CHR′, where R is alkyl and R′ is alkyl or hydrogen are satisfacory feed compounds for the process. Preferably the carbon atom content of the alkene is less than about 20.

Among other factors, the present invention is based on my finding that using the process of the present invention, particularly including the use of a composition consisting essentially of molybdenum(VI) oxide, results in good yields of ketones, and the molybdenum(VI) oxide composition exhibits exceedingly high activity, resulting in good yields even at relatively low temperature and contact times.

By a molybdenum(VI)-oxygen compound, as used herein, is meant a member of the class of compounds which includes molybdic oxide, molybdic acid, isopolymolybdic acid, the ammonium salts of these acids, the hydrated modifications of the foregoing compounds and mixtures of these compounds. The numeral VI has the ordinary meaning and refers to the +6 oxidation state for the molybdenum. The molybdenum(VI) oxide used in the present invention consists essentially of molybdenum(VI) oxide and is essentially free of bismuth. Thus, compositions such as the bismuth-containing compositions discussed in the previously mentioned Foreman and Hucknall references are excluded.

The molybdenum(VI) oxide composition used in the present invention facilitates and accelerates the reaction in the process of the present invention, and in that sense is a catalyst, but it is also believed to be a reactant in the present invention, as described hereinbelow.

As will be evident from the further description given herein, as the oxidation reaction proceeds the valence level of the starting molybdenum(VI) oxide compound will drop because of reduction by interaction with the alkene in the production of the ketone product.

In a preferred embodiment of my invention, a gaseous mixture of an alkene, for example 1-hexene, and water in the mol ratio 1 to 10, respectively, is contacted with molybdenum trioxide supported on a carrier, for example alumina, as in a fixed-bed reactor maintained at a temperature of about 300° C. As the reaction proceeds, the molybdenum of the oxide is reduced and the production of ketones slows down correspondingly. The feed to the reactor is continued until the conversion of the 1-hexene to ketones drops to an uneconomic level, for example about 50% of the original value, and then is discontinued. The reduced molybdenum oxide is then reoxidized by passing an oxygen-containing gas, preferably air, into contact with the fixed bed. After the regeneration, which is an exothermic reaction, the temperature of the fixed bed is adjusted to the operating temperature by a suitable means, for example by the introduction of steam, and the cycle is repeated. The aqueous and organic phases of the condensed product are separated, the former being recycled to the process and the latter, which is a mixture of 1-hexene and ketones, is separated by a suitable means, for example by distillation. The separated and unconverted alkene feed is returned to the process.

The conversion may be summarized as follows:

  1)

but the actual mechanism of the reaction is probably more involved than the equation suggests, particularly since water is required in order for the reaction to progress. In addition, concurrent isomerization of the double bond of the alkene occurs and the resulting ketone, particularly in a continuous process which includes recycle of unconverted alkene, will be mainly the product of the isomerized alkene. The major product from a single pass is generally that derived from the original feed.

The conversion of alkene to ketone in the subject process can take place with the water and alkene in the liquid or vapor phase. A hydrated molybdenum(VI)-oxygen compound is soluble in water to a limited degree, and thus a portion of the conversion may be via a homogeneous reaction system. The bulk of the reaction, however, appears to occur via a heterogeneous solid-liquid, or solid-gas, system. Therefore, the reaction may be effected in conventional fixed-bed, fluid-bed or slurry-type systems. Continuous operation employing the heterogeneous solid-gas reaction system with the hydrated compound in a fixed bed or fluid bed is the preferred process mode.

For efficient utilization, the molybdenum(VI) compound is desirably in the form of high surface area such as a finely divided powder or a coating upon a porous surface. However, any form of molybdenum(VI) compound, either pure or diluted with an inert diluent, supported or unsupported, can be used in this process. For example, when molybdenum trioxide is contacted with water under the process conditions, a rapid interaction occurs which may be summarized as follows:

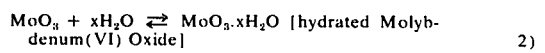  2)

Similarly, molybdenum(VI)-oxygen compounds in general, including those containing some molybdenum in a reduced oxidation state, yield the hydrated molybdenum(VI)-oxygen component useful in the present process upon contact with water under the conditions of the invention. In the case of the ammonium salts, apparently a hydrolytic equilibrium involving the acid forms is involved.

Representative molybdenum(VI)-oxygen compounds useful in the process include molybdic acid, isopolymolybdic acid, molybdenum(VI) hydrates, $MoO_3 \cdot H_2O$, $MoO_3 \cdot 2H_2O$, the 85% molybdic acid of commerce, ammonium paramolybdate, ammonium isopolymolybdate [$(NH_4)_2Mo_2O_7$], polymeric molybdic acid, and the like.

The reaction takes place over a range of temperatures and the rate increases in the usual manner as the temperature is raised. Broadly, a temperature in the range 200° to 400° C is satisfactory. Better results are, in general, experienced in the range from 250° to 350° C. Above about 350° C, concurrent reactions which result in the formation of by-products, including rearranged hydrocarbons and thermal degradation products become significant. In large part, these undesirable side reactions are minimized by increasing the water content of the process feed and the system pressure, and thus reaction temperatures in the range 350° to 400° C may also be satisfactorily employed in the process.

Suitable reaction periods vary broadly, depending upon the temperature in particular and secondarily upon ordinary factors such as mixing efficiency and the like. In general, a satisfactory result for a batch process may be achieved in a period in the range from about 0.1 to 10 hours. For a continuous process, a satisfactory result may be achieved with a contact time from about 1 second to 1 hour.

The function of water in the process appears to be complex and is not clear. In the absence of water, little or none of the desired ketone product is produced. In the presence of a minor amount of water, less than one mol per mol of the alkene, an appreciable amount of ketone is produced together with a substantial amount of undesirable by-product. Satisfactory relative amounts of water are in the range from about 1 to 100 mols. In general, when the amount of water is in the range 3 to 10, the yield of ketone product is excellent. Larger relative amounts of water, that is 20 mols and higher, are operational and, in general, more or less beneficial, but the incremental benefit tends to be offset by the increased processing cost per unit of product. Usually the employment of a feed containing as much as 100 mols of water per mol of alkene feed is uneconomical.

The process of the invention is in general effective for the conversion of an alkene carbon-carbon double bond to a ketonic carbonyl group, for example

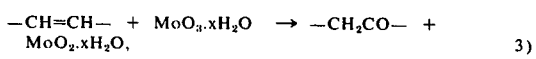  3)

provided that the alkene is not a solid (i.e., is a liquid and/or a gas) at a temperature within the process temperature range and that neither of the carbon atoms of the double-bond pair is a tertiary carbon. Both carbon atoms of the double bond may be secondary carbon, or one may be a primary and the other a secondary carbon.

Alkene hydrocarbon feeds of the formula $RCH=CHR'$ (R is an alkyl group and R' is hydrogen or an alkyl group) are in general preferred for use as process feeds and are contemplated herein, provided that the alkene is not a solid at a temperature within the range 200°–400° C, as noted above; and of these, the n-alkenes having a carbon atom content in the range from 3 to about 20, and particularly 3 to 10, are preferred. The feed may be a single molecular species or a mixture.

Representative alkenes useful as feeds for my process include propene, 1-butene, 2-butene, 1-pentene, 2-pentene, 4-methyl-1-pentene, 1-hexene, 2-hexene, 3-hexene, 3-ethyl-1-hexene, 1-octene, 1-nonene, 1-decene, 3-decene, 5-isopropyl-1-decene, 4-cyclohexyl-1-butene, 8,8-dimethyl-2-nonene, 4-ethyl-1-dodecene, 5-octadecene, 2-cyclohexyl-6-undecene 1-hexadecene, 4-phenyl-1-butene, 1-eicosene, and the like alkenes, that is, an alkene hydrocarbon which contains the structural grouping

or which would contain this configuration by the shift of a single hydrogen atom of the molecule, for example:

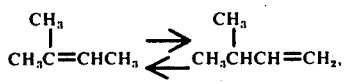

since such compounds appear to be isomerized under the conditions of the process.

Pressure is not a critical process variable. Thus useful conversions occur with the reaction system under atmospheric, subatomospheric or superatmospheric pressure conditions. However, better results in general have been experienced with the system under a superatmospheric pressure. In view of the relatively high cost for pressure reactors, the satisfactory use of reaction pressures in excess of 340 atmospheres is deemed unlikely. For the liquid-phase mode of this invention, the range from 20 to about 200 atmospheres is preferred. For the vapor-phase mode, operation in the range 1 to about 100 atmospheres is satisfactory and from 1 to about 20 atmospheres is preferred.

EXAMPLES

The following examples further illustrate the invention.

EXAMPLES 1-2

A mixture of water vapor and propene was introduced into contact with a bed of a commercially available composite of 10 weight percent of molybdenum trioxide on alumina under the following conditions:

|  | 1 | 2* |
|---|---|---|
| Temperature, ° C | 300 | 325 |
| Water:alkene, mol ratio | 2.5 | 10 |
| Pressure, psig | 75 | 75 |
| WHSV, hr.$^{-1}$ | 6.8 | 1.7 |

*For Example 2, the used molybdenum oxide from Example 1 was regenerated prior to use by a stream of air at about 375° C.

The results were as follows:

| Example | 1 | 2 |
|---|---|---|
| Initial conversion to acetone, % | 4.9 | 18 |
| Initial conversion to other condensable products | nil | nil |
| Conversion to acetone after 1 hr., % | 1.1 | 3.7 |
| Conversion to other condensable products after 1 hr., % | 0.1 | nil |

These data demonstrate that alkenes are converted to ketones in the present process and that low space velocities and a larger water-to-olefin mol ratio is beneficial in increasing conversion and minimizing side products.

EXAMPLE 3

A bed of supported solid molybdenum(VI) oxide was prepared by impregnating 100 g. of extruded alumina having a 3/32 inch diameter with a solution of 13.6 g of ammonium molybdate in 70 ml of water, evaporating, drying at 100° C, and heating the impregnate at 500° C for 5 hours. The bed was reduced by normal operation, in the course of which the color changed from yellow to dark grey. The oxide was reoxidized at an initial temperature of about 300° C, by contact with oxygen gas. The final temperature during the regeneration was 600° C. The oxygen treatment was continued until the solid regained the yellow color of fully oxidized molybdenum trioxide. Then the bed was cooled to 225° C and a mixture of water and 1-hexene at a liquid volume ratio of 3 to 1, respectively, was vaporized and passed into contact with the oxide at atmospheric pressure (WHSV = 0.4 hr.$^{-1}$, mol ratio of water to 1-hexene = 20). The organic condensate contained 4.7% of 2-hexanone and 3.1% of 3-hexanone. The balance was undifferentiated $C_6$ hydrocarbons except for 0.3% of other condensable products.

The bed was again regenerated by contact with a stream of oxygen gas at 400° C for a period of 3 hours. A water-and-hexene feed mixture was then passed as before into contact with the bed at 284° C yielding 4.8% of 2-hexanone, 3.7% of 3-hexanone, and 0.4% of other condensable products.

These data demonstrate that the hydrated molybdenum(VI) oxide can be effectively regenerated in a variety of ways.

EXAMPLE 4

1-Hexene was converted as in Examples 1 and 2 using a freshly prepared bed of molybdenum(VI) oxide, except that the WHSV was 0.3 hr.$^{-1}$, the temperature employed was 292° C, the pressure was atmospheric, and the mol ratio of water to 1-hexene was 20 to 1, with the following results:
2-Hexanone — 6.5%
3-Hexanone — 6.0%
Other condensable products — 1.0%.

EXAMPLE 5

Examples 1 and 2 were repeated except that the alkene was 1-hexene, the pressure was atmospheric, the temperature was 280° C, the WHSV was 0.9 hr.$^{-1}$, and the mol ratio of water to 1-hexene was 10. The initial product stream was 5.6% of 2-hexanone, 4.8% of 3-hexanone and 1.0% of other condensable products. After an on-stream reaction period of 2 hours, the product stream contained 2.7% of 2-hexanone, 1.5% of 3-hexanone, and 0.2% of other condensable products. After regeneration of the bed to molybdenum(VI) oxide and the repetition of the above conditions, the result obtained was for all practical purposes identical.

These data demonstrate that at a water-to-alkene mol ratio of 10 to 1, the product selectivity of the process for ketone production is very good. In addition, as was also demonstrated in the foregoing examples, the conversion of alkene to ketone decreases with time, but the reduced molybdenum(VI) oxide can be readily and fully regenerated to its original activity and selectivity.

EXAMPLES 6-19

In the following examples, 1-hexene, water, and a hydratable molybdenum(VI)-oxygen compound, as noted in the following Table, were charged to a 15-ml stainless-steel reactor. For the indicated periods, the reactor and its contents, as noted in the Table, were maintained with mixing at about 350° C. The pressure (estimated) in the reactor was in the range 160-200 atmospheres and was sufficient to insure the presence of an aqueous liquid phase. The results are listed in the Table.

TABLE

| Ex. No. | Vol of 1-Hexene (ml) | Vol of Water (ml) | Wt. (g) Molybdic Acid | Wt. (g) Molybdenum Trioxide | Wt. (g) Ammonium Molybdate | Time (Hr.) | Wt. % of Products[X] 2-Hexanone | 3-Hexanone | 2-Hexanol | 3-Hexanol | Other |
|---|---|---|---|---|---|---|---|---|---|---|---|
| 6 | 0.7 | 4 | 0.5 | | | 0.25 | 4.5 | 2.3 | 0.8 | 0.6 | 0.5 |
| 7 | 0.7 | 4 | 0.5 | | | 1 | 7.6 | 4.8 | 1.0 | 0.6 | 0.7 |
| 8 | 0.7 | 4 | 0.5 | | | 3 | 10.1 | 6.7 | 0.8 | 0.6 | 0.8 |
| 9 | 0.7 | 2 | 0.5 | | | 1 | 3.7 | 1.0 | 1.2 | 0.4 | 0.1 |
| 10 | 0.7 | 3 | 0.5 | | | 1 | 5.2 | 2.5 | 0.9 | 0.6 | 0.4 |
| 11 | 0.7 | 4 | 0.5 | | | 1 | 7.6 | 4.8 | 1.0 | 0.6 | 0.7 |
| 12 | 0.7 | 5 | 0.5 | | | 1 | 9.7 | 5.8 | 0.8 | 0.6 | 1.0 |
| 13 | 0.5 | 4 | 0.1 | | | 1 | 1.2 | 0.5 | 0.7 | 0.4 | 0.3 |
| 14 | 0.5 | 4 | 0.5 | | | 1 | 9.6 | 6.2 | 1.0 | 0.8 | 0.8 |
| 15 | 0.5 | 4 | 1.5 | | | 1 | 18.9 | 10.9 | 0.6 | 0.5 | 1.8 |
| 16 | 1.0 | 4 | | 0.5 | | 1 | 2.7 | 1.5 | 0.8 | 0.6 | 0.5 |
| 17 | 1.0 | 4 | 0.5 | | | 1 | 7.6 | 4.0 | 1.2 | 0.8 | 0.5 |
| 18 | 0.7 | 2 | | | 0.5 | 3 | 3.7 | 1.0 | 1.1 | 0.4 | 0.1 |
| 19 | 0.7 | 2 | 0.5 | | | 3 | 5.3 | 1.4 | 0.9 | 0.5 | 0.2 |

(X) The balance of product stream was unconverted olefinic hydrocarbon plus a minor amount of saturated hydrocarbon.

The foregoing data include the demonstration that good results are obtained with the reaction system under a pressure sufficient to insure the presence of an aqueous liquid phase. It also illustrates that a variety of molybdenum(VI)-oxygen compounds may be employed in the process as the source of the hydrated molybdenum(VI) oxide, that the hydrated molybdenum(VI) oxide need not be placed upon a supporting material, and that the use of appreciable water-to-olefin ratios, for example of the order of 10 to 1 and higher, is desirable.

EXAMPLE 20

In the manner and in the unit described in Examples 6–19, an n-pentene-n-pentane mixture (approximately 16% n-pentenes) was employed as feed in the process. The charge consisted of 2 ml of the pentene-pentane mix, 4 ml of water and 0.5 g of molybdic acid. After 3 hours at about 250° C, the resulting product mixture contained 2.7% of pentanones, 0.1% of pentanols, and no trace of other oxygenated product, i.e., a 14% conversion of the pentenes.

The example illustrates that except for the dilution effect the presence of large amounts of inert diluents does not adversely affect the conversion of an olefinic hydrocarbon feed.

The analyses for the examples described herein were obtained by the use of chromatographic means and appropriate standards.

The foregoing examples demonstrate that the contacting of an alkene-water mixture with hydrated molybdenum(VI)-oxygen compound at an elevated temperature results in the conversion of the alkene to one or more ketones having the same carbon atom content as the alkene feed to the process.

I claim:

1. A process for the conversion of an alkene to a ketone which comprises contacting, at a temperature between about 200° and 400° C, a mixture consisting essentially of water and said alkene with a composition consisting essentially of hydrated molybdenum(VI) oxide wherein said alkene is a gas or liquid at said temperature and wherein the carbon-carbon double bond carbon atoms of said alkene are both secondary carbons or one is secondary and the other is primary carbon, and wherein said mixture has a mol ratio of water to alkene between about 1:1 and 100:1.

2. A process in accordance with claim 1 wherein said temperature is between about 250° and 350° C and wherein the alkene has a carbon atom content less than about 20.

3. A process in accordance with claim 2 wherein said ratio is about 3:1 to 10:1.

4. A process in accordance with claim 1 wherein said molybdenum oxide is disposed upon an alumina support.

5. A process for the production of a ketone which comprises heating a mixture consisting essentially of an alkene feed, a composition consisting essentially of hydrated molybdenum(VI) oxide, and water at a temperature between about 200° and 400° C, wherein the mol ratio of water to the alkene in said mixture is between about 1:1 and 100:1, wherein said feed is one or more compounds of the formula RCH=CHR' in which R is an alkyl group and R' is hydrogen or an alkyl group, and wherein said feed is a liquid or gas at the process temperature.

6. A process in accordance with claim 5 wherein said feed is one or more n-alkenes having a carbon atom content less than about 20 carbon atoms, said temperature is between about 250° and 350° C, and said mol ratio is between about 3:1 and 10:1.

7. A process in accordance with claim 5 wherein said process is effected at a system pressure between about 1 and 200 atmospheres.

8. A process in accordance with claim 5 wherein said molybdenum oxide is disposed upon an alumina support.

9. A process in accordance with claim 5 wherein said heating is continued until the reaction rate is about one-half of the original value.

10. A process for the production of a hexanone mixture which comprises heating a mixture consisting essentially of 1-hexene, water and molybdenum trioxide at a temperature of about 300° C, wherein the mol ratio of the hexene to water is about 1 to 10, wherein said heating is for a period between about 0.1 and 10 hours.

11. A continuous cyclic process for the production of a ketone which comprises reacting a mixture consisting essentially of an alkene feed, a composition consisting essentially of hydrated molybdenum(VI) oxide and water by heating at a temperature between about 200° and 400° C and a pressure between 1 and about 10 atmospheres wherein the mol ratio of water to said alkene is between about 3:1 and 10:1, wherein said cyclic process comprises alternately effecting said reaction and regenerating said molybdenum compound by contacting the compound with an oxygen-containing gas consisting essentially of molecular oxygen, and wherein said feed contains one or more n-alkenes having a carbon atom content between 3 and about 10.

* * * * *